United States Patent
Yamada

(10) Patent No.: US 10,799,100 B2
(45) Date of Patent: Oct. 13, 2020

(54) IMAGE PROCESSING DEVICE, METHOD, AND PROGRAM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 466 days.

(21) Appl. No.: 15/695,588

(22) Filed: Sep. 5, 2017

(65) Prior Publication Data

US 2017/0360285 A1  Dec. 21, 2017

Related U.S. Application Data

(63) Continuation of application No. PCT/JP2016/054387, filed on Feb. 16, 2016.

(30) Foreign Application Priority Data

Mar. 18, 2015 (JP) ................. 2015-054179

(51) Int. Cl.
*A61B 1/05* (2006.01)
*A61B 1/267* (2006.01)
(Continued)

(52) U.S. Cl.
CPC .............. *A61B 1/05* (2013.01); *A61B 1/0005* (2013.01); *A61B 1/00009* (2013.01);
(Continued)

(58) Field of Classification Search
CPC ....... A61B 1/0005; A61B 1/2676; A61B 1/31; A61B 5/06

See application file for complete search history.

(56) References Cited

U.S. PATENT DOCUMENTS 8,454,497 B2 * 6/2013 Tanaka ............... A61B 1/00006
600/118
9,326,660 B2 * 5/2016 Akimoto ............ A61B 1/00009
(Continued)

FOREIGN PATENT DOCUMENTS

JP   2004-105725 A   4/2004
JP   2005-131318 A   5/2005
(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2016/054387, dated Sep. 28, 2017, with an English translation of the Written Opinion.
(Continued)

*Primary Examiner* — Timothy J Neal
*Assistant Examiner* — Jae Woo
(74) *Attorney, Agent, or Firm* — Birch, Stewart, Kolasch & Birch, LLP

(57) ABSTRACT

An image processing device for an endoscope in which an operation of bending a distal end portion only within one endoscope bending plane including an axis of the distal end portion is allowed, the image processing device having a processor configured to acquire information of a course along which the endoscope travels in the luminal structure, the course being set based on a three-dimensional image indicating the luminal structure, and calculate a first rotation angle of the endoscope at a first branch in the course, the first rotation angle being an angle to match the one endoscope bending plane where the distal end portion is allowed to bend with a plane of the first branch, by a operation of rotation.

19 Claims, 6 Drawing Sheets

(51) Int. Cl.
- *A61B 1/31* (2006.01)
- *A61B 1/00* (2006.01)
- *A61B 5/06* (2006.01)
- *G06T 7/00* (2017.01)
- *A61B 34/20* (2016.01)
- *A61B 1/005* (2006.01)

(52) U.S. Cl.
CPC .............. *A61B 1/2676* (2013.01); *A61B 1/31* (2013.01); *A61B 5/06* (2013.01); *G06T 7/0012* (2013.01); *A61B 1/005* (2013.01); *A61B 34/20* (2016.02); *G06T 2207/10072* (2013.01)

(56) References Cited

U.S. PATENT DOCUMENTS

| | | |
|---|---|---|
| 2004/0249267 A1 | 12/2004 | Gilboa |
| 2008/0234700 A1 | 9/2008 | Trovato et al. |
| 2011/0234780 A1* | 9/2011 | Ito ............................ A61B 1/05 348/65 |
| 2015/0272427 A1* | 10/2015 | Haque .................. A61B 1/0005 348/65 |
| 2018/0140168 A1* | 5/2018 | Haraguchi ............. A61B 1/018 |

FOREIGN PATENT DOCUMENTS

| | | |
|---|---|---|
| JP | 2009-511155 A | 3/2009 |
| JP | 2009-254837 A | 11/2009 |

OTHER PUBLICATIONS

International Search Report (Form PCT/ISA/210) for International Application No. PCT/JP2016/054387 dated May 17, 2016, with an English translation.

* cited by examiner

IMAGE PROCESSING DEVICE, METHOD, AND PROGRAM

CROSS-REFERENCE TO RELATED APPLICATIONS

This application is a Continuation of PCT International Application No. PCT/JP2016/054387 filed on Feb. 16, 2016, which claims priority under 35 U.S.C § 119(a) to Patent Application No. 2015-054179 filed in Japan on Mar. 18, 2015, all of which are hereby expressly incorporated by reference into the present application.

BACKGROUND OF THE INVENTION

1. Field of the Invention

The present invention relates to an image processing device, method, and a non-transitory computer readable recording medium storing a program in which a parameter value regarding an endoscope operation for advancing an endoscope along a predetermined course in a luminal structure is calculated from a three-dimensional image indicating the luminal structure.

2. Description of the Related Art

In recent years, a technology for performing observation or treatment on a tubular structure such as a large intestine or a bronchial tube of a patient using an endoscope has attracted attention. JP2009-254837A discloses a technology for supporting an operation of an endoscope by an operator by presenting various kinds of information for guiding a distal end portion of the endoscope to a desired position in a luminal structure. Further, JP2009-511155A discloses a technology for calculating up, down, right, and left bending angles of a distal end portion at each position on a course for advancing an endoscope along a desired course in a luminal structure in a case where an operation of bending the distal end portion in an up-down direction and a left-right direction is allowed in the endoscope.

SUMMARY OF THE INVENTION

Incidentally, in an endoscope such as an endoscope for a bronchial tube in which an operation of bending a distal end portion only within one plane is allowed, the endoscope cannot be advanced in a desired direction only by an operation of bending the distal end portion. In this case, it is necessary to match the one plane within which the operation of bending the distal end portion is allowed with the desired direction by rotating the endoscope around an axis before the bending operation. In this case, the endoscope is usually rotated to a rotation direction (clockwise or counterclockwise direction) in which the amount of rotation necessary for a rotation operation is smaller. For example, in a case where the endoscope needs to be rotated by 50° in the clockwise direction or 130° in the counterclockwise direction to advance the endoscope by bending the distal end portion, the endoscope is rotated by 50° in the clockwise direction since the rotation amount of 50° is smaller than the rotation amount of 130°.

However, in this method, the endoscope may be continued to rotate in one rotation direction and the endoscope may rotate in the one rotation direction beyond a movable range of a wrist. In this case, the operability is poor since an operator of the endoscope is required to grip the endoscope again.

An object of the present invention is to provide an image processing device, method, and a non-transitory computer readable recording medium storing a program that reduce trouble of an operator gripping an endoscope again and improve operability in a case where the endoscope is an endoscope in which an operation of bending a distal end portion only within one plane is allowed in view of the above circumstances.

An image processing device of the present invention is an image processing device for an endoscope in which predetermined operations are allowed, the predetermined operations being an advancing and retreating operation in an axial direction, an operation of rotation around an axis, and an operation of bending a distal end portion only within one endoscope bending plane including an axis of the distal end portion. The image processing device comprises a processor configured to: acquire information of a course along which the endoscope travels in a luminal structure, the course being set based on a three-dimensional image indicating the luminal structure and including a plurality of branches, each of the plurality of branches representing a change in direction, and calculate rotation angles of the endoscope for the operations of rotation at the plurality of branches, the rotation angles being angles for matching the one endoscope bending plane, which the distal end portion is allowed to bend, with a plane corresponding to the each of the plurality of branches. The processor calculates a first rotation angle at each branch for each of the plurality of branches such that a sum of the first rotation angle and a cumulative rotation angle fall within a predetermined angle range, the cumulative rotation angle being a total sum of rotation angles of the endoscope calculated for each of the branches from an entrance of the course to each branch.

Here, the clockwise direction and the counterclockwise direction around the axis mean a clockwise direction and a counterclockwise direction when viewed from a base end side of an endoscope.

In the image processing device of the present invention, the predetermined angle range is from −90° to +90°, in a case where one of a clockwise direction and a counterclockwise direction around the axis is set to a positive angle and the other is set to a negative angle.

In the image processing device of the present invention, the luminal structure may be a luminal organ of a human body and in a case where two rotation angles for both the clockwise direction and the counterclockwise direction can fall within a predetermined angle, the processor is further configured to calculate one of the two rotation angles as the first rotation angle according to information of a direction vector from a dorsal side to a ventral side of the human body and an up direction vector of an image captured by the endoscope after the rotation operation with the first rotation angle.

Here, the up direction of the image means an up direction (direction from bottom to top) in an up-and-down direction (vertical direction) of the image. [0012].

In the image processing device of the present invention, in a case where two rotation angles can be the first rotation angle, the processor is configured to calculate one of the two rotation angles as the first rotation angle so that an absolute value of a second rotation angle at a second branch is minimized, the second branch is a branch where the endoscope advances from the first branch along the course.

In the image processing device of the present invention, the processor is further configured to acquire a position and a posture of the endoscope in the course; and generate a virtual endoscopic image from the three-dimensional image using the position and the posture.

In the image processing device of the present invention, the processor is further configured to acquire a position of the endoscope in the course; and display the first rotation angle on a display unit according to the position of the endoscope in the course when the endoscope advances along the course.

An image processing method of the present invention is an image processing method for an endoscope in which predetermined operations are allowed, the predetermined operations being an advancing and retreating operation in an axial direction, an operation of rotation around an axis, and an operation of bending a distal end portion only within one plane including an axis of the distal end portion. The image processing method comprises acquiring information of a course along which the endoscope travels in the luminal structure, the course being set based on a three-dimensional image indicating the luminal structure, and the course including a plurality of branches, each of the plurality of branches representing a change in direction; and calculating rotation angles of the endoscope for the operations of rotation at each of the plurality of branches, the rotation angles being angles for matching the one endoscope bending plane, which the distal end portion is allowed to bend, with a plane corresponding to the each of the plurality of branches. A first rotation angle at each branch of the plurality of branches is calculated for each of the plurality of branches such that a sum of the first rotation angle and a cumulative rotation angle fall within a predetermined angle range, the cumulative rotation angle being a total sum of rotation angles of the endoscope calculated for each of the branches from an entrance of the course to each branch.

A non-transitory computer readable recording medium is provided storing an image processing program for an endoscope in which predetermined operations are allowed, the predetermined operations being an advancing and retreating operation in an axial direction, an operation of rotation around an axis, and an operation of bending a distal end portion only within one endoscope bending plane including an axis of the distal end portion. The image processing program causes a computer to execute a process of acquiring information of a course along which the endoscope travels in the luminal structure, the course being set based on a three-dimensional image indicating the luminal structure, and the course including a plurality of branches, each of the plurality of branches representing a change in direction; and calculating rotation angles of the endoscope for the operations of rotation at each of the plurality of branches, the rotation angles being angles for matching the one endoscope bending plane, which the distal end portion is allowed to bend, with a plane corresponding to the each of the plurality of branches. The first rotation angle is calculated for each branch of the plurality of branches such that a sum of the first rotation angle and a cumulative rotation angle fall within a predetermined angle range, the cumulative rotation angle being a total sum of rotation angles of the endoscope calculated for each of the plurality of branches from an entrance of the course to each branch.

In the image processing method and program of the present invention, the angle range may be from −90° to +90°, in a case where one of a clockwise direction and a counterclockwise direction around the axis is set to a positive angle and the other is set to negative angle.

The image processing program of the present invention usually includes a plurality of program modules, and each process is realized by one or a plurality of program modules. A group of program modules is recorded on a recording medium such as a CD-ROM or a DVD or recorded in a downloadable state in a storage attached to the server computer or a network storage, and is provided to a user.

In the image processing device, method, and program of the present invention, on the assumption that an advancing and retreating operation in an axial direction, an operation of rotation around an axis, and an operation of bending a distal end portion only within one plane including an axis of the distal end portion are allowed in an endoscope, the parameter value regarding the endoscope operation for advancing the endoscope along a predetermined course in the luminal structure is calculated from the three-dimensional image indicating the luminal structure. Specifically, when one of a clockwise direction and a counterclockwise direction around the axis is set to positive, the other is set to negative, and a rotation angle of the endoscope due to the rotation operation at an arbitrary position on the course is calculated as a parameter value regarding the rotation operation, the rotation angle of the endoscope due to the rotation operation at the position of the target is calculated so that a sum of a cumulative total of rotation angles of the endoscope due to a rotation operation performed until the distal end portion arrives at the position of the target after the distal end portion is inserted into the luminal structure, and the rotation angle of the endoscope due to the rotation operation at the position of the target falls within the predetermined angle range. Thus, an appropriate angle range for which a movable range of a wrist or the like is taken into consideration is determined in advance such that the rotation of the endoscope due to the rotation operation is performed only within the angle range, and it is possible to reduce trouble of an operator gripping an endoscope again and improve operability. Further, it is possible to reduce a burden on patients by shortening an examination time with the improved operability.

DESCRIPTION OF THE PREFERRED EMBODIMENTS

Figure 1:
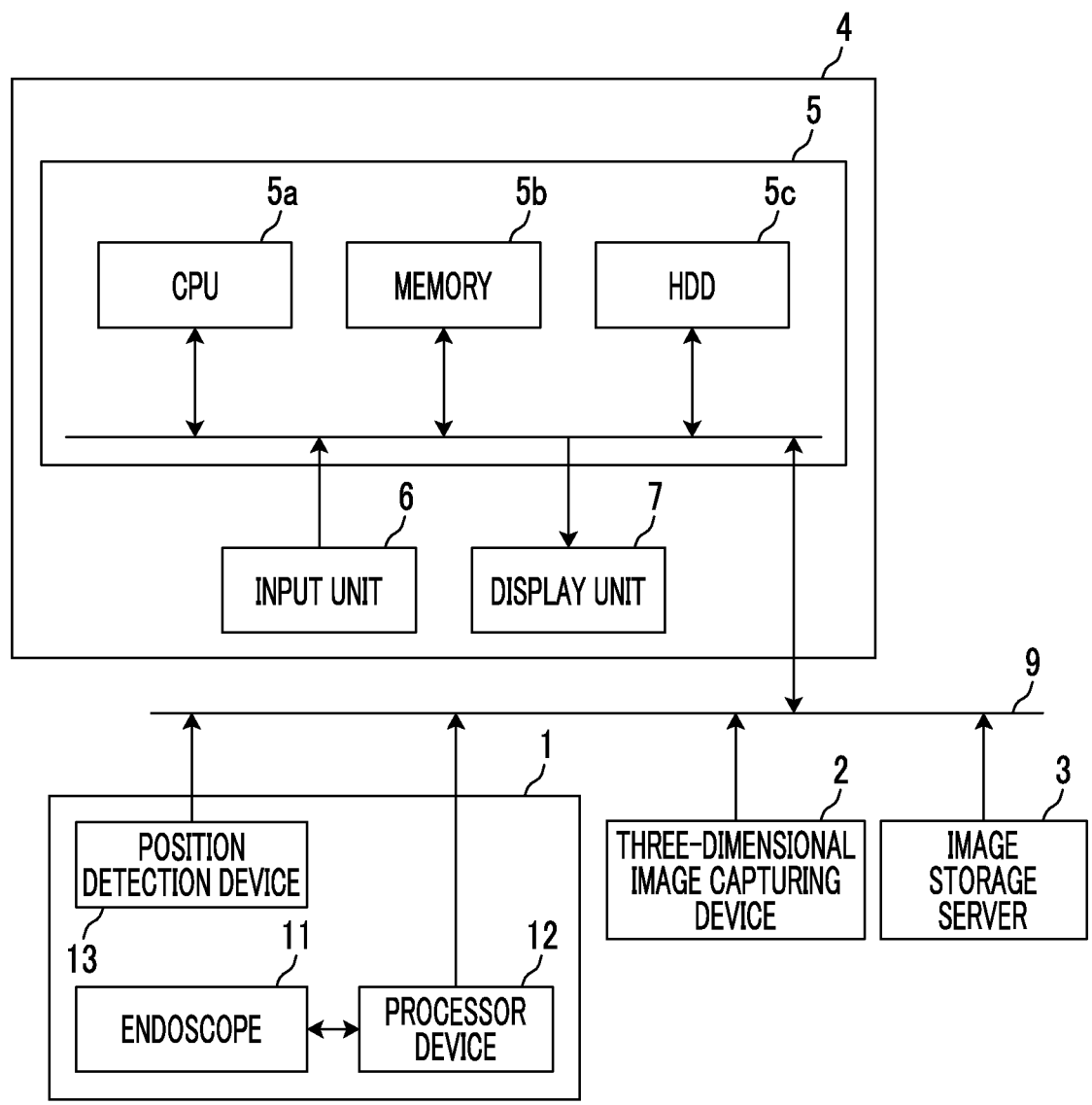
FIG. 1 is a diagram illustrating a schematic configuration of an image processing system including an embodiment of the present invention.

Hereinafter, an image processing system including an embodiment of an image processing device, method, and program of the present invention will be described with reference to the drawings. FIG. 1 is a block diagram illustrating a schematic configuration of an image processing system. As illustrated in FIG. 1, in this system, an endoscope device 1, a three-dimensional image capturing device 2, an image storage server 3, and an image processing device 4 are communicably connected over the network 9.

The endoscope device 1 includes an endoscope 11 that is inserted into a bronchial tube (a luminal structure) of a subject and images the inside of the bronchial tube, a processor device 12 that generates an image of the inside of the bronchial tube (hereinafter referred to as "endoscopic image") on the basis of an imaging signal obtained by imaging in the endoscope 11, and a position detection device 13 that detects a position of a distal end of the endoscope 11 in the bronchial tube.

The endoscope 11 is configured so that an advancing and retreating operation in an axial direction, an operation of rotation around an axis, and an operation of bending a distal end portion only within one plane including an axis of the distal end portion are allowed. The endoscope 11 includes an operation unit for operating an operation of the endoscope on the base end side, and has a mechanism for bending the distal end portion in a predetermined angle range within one plane including an axis of the distal end portion according to an operation input from the operation unit.

The processor device 12 converts the imaging signal obtained by imaging in the endoscope 11 into a digital image signal, performs correction of image quality through digital signal processing such as white balance adjustment and shading correction, and generates the endoscopic image. The generated endoscopic image is transmitted to the image processing device 4 via the image storage server 3 or directly.

The position detection device 13 detects a characteristic shape of a distal end of the endoscope using, for example, an echo device having a detection area in a three-dimensional coordinate system with a specific position of the subject as a reference point, to detect the position of the distal end of the endoscope in the bronchial tube. Information on the detected position is transmitted to the image processing device 4.

The three-dimensional image capturing device 2 is a device that images an inspection target part of the subject to generate a three-dimensional image representing the inspection target part. Specifically, the three-dimensional image capturing device 2 is a computed tomography (CT) device, a magnetic resonance imaging (MRI) device, or the like. The generated three-dimensional image is transmitted to the image storage server 3 and stored. In this embodiment, the three-dimensional image capturing device 2 generates the three-dimensional image in which a chest portion including the bronchial tube is captured.

The image storage server 3 is a computer that stores and manages data, and includes an external storage device and database management software. The image storage server 3 acquires image data such as the endoscopic image acquired by the endoscope device 1 and the three-dimensional image generated by the three-dimensional image capturing device 2 via a network, stores the image data in a recording medium such as an external storage device, and manages the image data.

The image processing device 4 is an image processing device in which an image processing program of the present invention installed in a computer (including a smartphone or a tablet computer). The image processing device 4 includes a device body 5 including a central processing unit (CPU) and the like, an input unit 6 that receives an input from a user, and a display unit 7 that performs a display. The input unit 6 is a mouse, a keyboard, a touch pad, or the like. The display unit 7 is a liquid crystal display, a touch panel, a touch screen, or the like.

The device body 5 includes a CPU 5a, a memory 5b, and a hard disk drive (HDD) 5c. The CPU 5a, the memory 5b, and the HDD 5c are connected to each other by a bus line. In the HDD 5c, the image processing program of the present invention and data referred to by the program are stored. The CPU 5a executes various processes using the memory 5b as a primary storage area according to the program stored in the HDD 5c.

Figure 2:
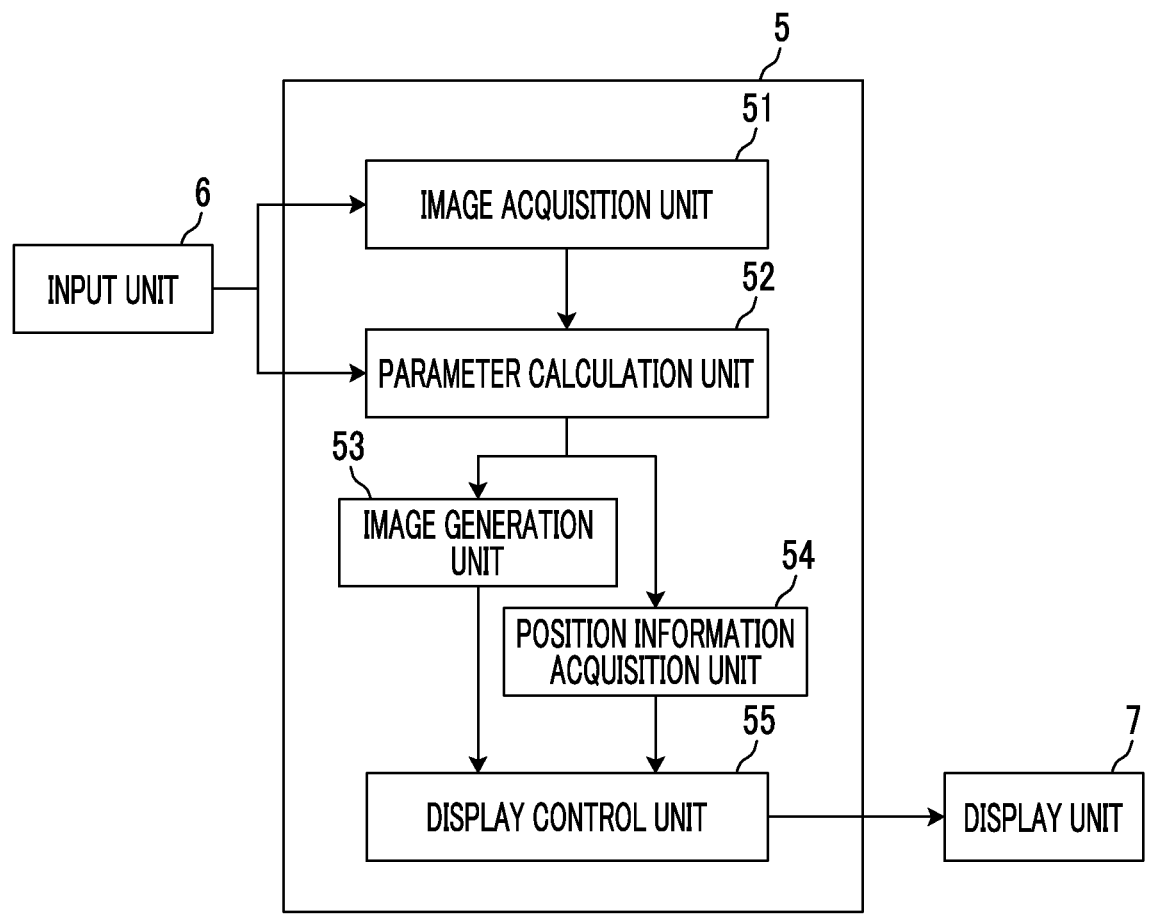
FIG. 2 is a block diagram illustrating functions provided in an image processing device in FIG. 1.

FIG. 2 is a functional block diagram illustrating functions of the image processing device 4. As illustrated in FIG. 2, the device body 5 of the image processing device 4 functions as an image acquisition unit 51, a parameter calculation unit 52, an image generation unit 53, a position information acquisition unit 54, and a display control unit 55 by the CPU 5a executing information processing according to the program stored in the HDD 5c.

The image acquisition unit 51 acquires the image data such as the endoscopic image generated by the endoscope device 1 and the three-dimensional image generated by the three-dimensional image capturing device 2 from the respective devices directly or via the image storage server 3. The image acquired by the image acquisition unit 51 is stored in the HDD 5c.

The parameter calculation unit 52 calculates a parameter value regarding an endoscope operation for advancing the endoscope along a predetermined course in the bronchial tube from the three-dimensional image acquired by the image acquisition unit 51. In this case, it is assumed that an advancing and retreating operation in an axial direction, an operation of rotation around an axis, and an operation of bending a distal end portion only within one plane including an axis of the distal end portion are allowed in an endoscope.

The parameter calculation unit 52 first extracts a three-dimensional graph structure of a bronchial tube area included in the three-dimensional image through image analysis and automatically or manually sets a course C into which the endoscope is inserted in the extracted graph structure. On the basis of information on the set course C, the parameter calculation unit 52 calculates parameter values regarding the advancing and retreating operation, the rotation operation, and the bending operation of the endoscope.

Figure 3:
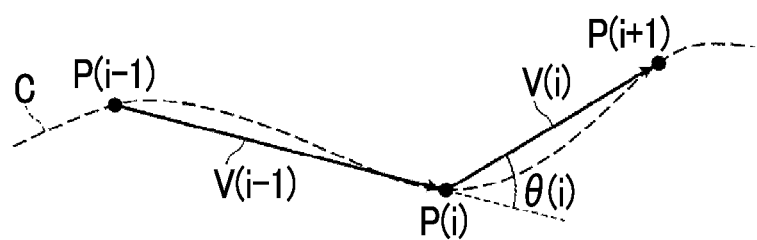
FIG. 3 is a diagram illustrating a method of calculating a bending angle in a bending operation of an endoscope.

Specifically, the parameter calculation unit 52 calculates an insertion length of the endoscope along the set course C as a parameter of the advancing and retreating operation. Further, the parameter calculation unit 52 calculates a bending angle of the endoscope corresponding to an angle of the bending at an arbitrary position at which the endoscope is bent by a branch or the like on the course C as a parameter of the bending operation at the position. More specifically, the parameter calculation unit 52 calculates an angle $\theta(i)$ formed by two vectors including a vector $V(i-1)$ from a position $P(i-1)$ of a previous bending operation on the course C to a position $P(i)$ on the course C and a vector $V(i)$ from the position $P(i)$ to a position $P(I+1)$ of a next bending operation on the course C as the angle of bending of the endoscope at the position $P(i)$, as illustrated in FIG. 3.

Figure 4:
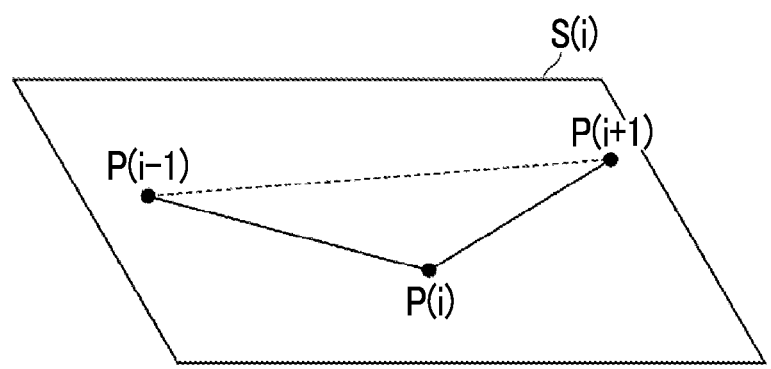
FIG. 4 is a diagram illustrating a plane passing through positions of a bending operation at three points on a course of a bronchial tube.
Figure 5:
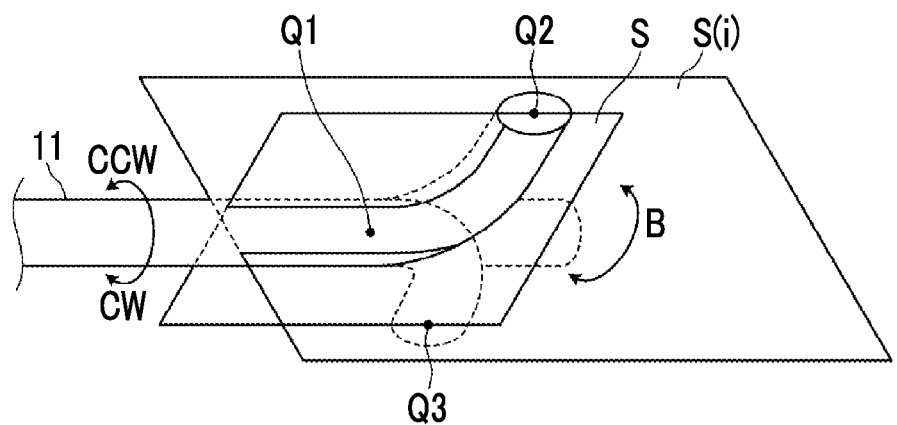
FIG. 5 is a diagram illustrating a plane within which an operation of bending a distal end portion of an endoscope is allowed.

Further, the parameter calculation unit 52 calculates the angle of the rotation in the rotation operation of the endoscope for further advancing the endoscope advanced to an arbitrary position $P(i)$ (or a position in front) at which the endoscope is bent due to a branch or the like on the course C, forward along the course C, as a parameter of the rotation operation at the position. Specifically, first, a plane S(i) passing through three points of a position P(i−1) of an immediately previous bending operation on the course C, a current position P(i), and a position P(i+1) of the next bending operation as illustrated in FIG. 4 is obtained. As illustrated in FIG. 5, in a state of the endoscope before the rotation operation, a plane S passing through three points of a position Q1 that is a fulcrum of the bending of the distal end portion and positions Q2 and Q3 of the distal end of the endoscope obtained when the distal end portion is bent by two arbitrary different bending angles is obtained. In FIG. 5, a direction in which the operation of bending the distal end portion can be performed is indicated by an arrow B. Similarly, in FIG. 6, a direction in which the operation of bending the distal end portion can be performed is indicated by an arrow B.

Figure 6:
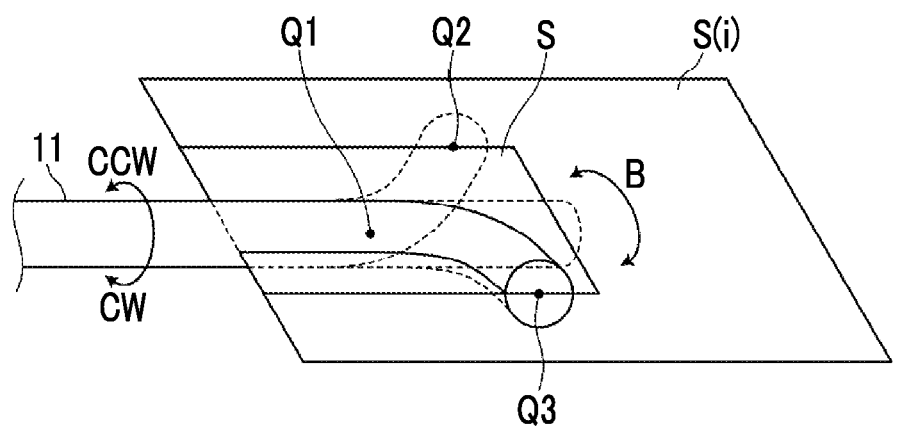
FIG. 6 is a diagram illustrating a method of calculating an angle of rotation in a rotation operation of the endoscope.

Further, as illustrated in FIG. 6, the parameter calculation unit 52 calculates a rotation angle (a first rotation angle) at the current position P(i) (a first branch) around the axis of the endoscope for causing the plane S to overlap the plane S(i), defining clockwise rotation around an axis of the endoscope is positive and counterclockwise rotation is negative. The rotation angle (a first rotation angle) is calculated so that a sum of the rotation angle and a cumulative rotation angle of the endoscope falls within a predetermined angle range Ra (for example, −90° to +90°). Here, the cumulative rotation angle is a total sum of rotation angles of the endoscope by operations of rotation performed at branches from an entrance of the course to the first branch. The rotation angle (a first rotation angle) is calculated as a parameter of the rotation operation at the position P(i). For example, consider a case where the predetermined angle range Ra is from −90° to +90° and a cumulative rotation angle of the endoscope by the rotation operation performed until the endoscope arrives at the position P(i) is +45°. In this case, the rotation angle of the endoscope at which the plane S overlap the plane S(i) is +50° (clockwise) or −130° (counterclockwise). Of the angles of +50° (clockwise) and −130° (counterclockwise), −130° that is a rotation angle of which a sum with the cumulative rotation angle falls within 90° to +90° is calculated as a parameter of the rotation operation at the position P(i).

Although a case where the angle range Ra is set to −90° to +90° has been described in the above description, the angle range Ra can be arbitrarily set automatically or manually, and can be appropriately changed as necessary. An example of the settable angle range Ra may include −Ta° to +Tb° (for example, −120° to +120°), where Ta and Tb are positive values exceeding 90, for example. Here, in setting of such an angle range, a sum of any of the clockwise and counterclockwise rotation angles at which the plane S overlap the plane S(i) and a cumulative rotation angle of the endoscope by the rotation operation performed until the distal end portion of the endoscope arrives at the current position P(i) may fall within the angle range Ra. For example, consider a case where the predetermined angle range Ra is from −120° to +120°, a cumulative total of the rotation angles of the endoscope due to the rotation operation performed up to the position P(i) is +45°. In this case, the rotation angle of the endoscope capable of causing the plane S to overlap the plane S(i) is +50° (clockwise) or −130° (counterclockwise) and a sum of any of the rotation angles (+50° and −130°) and the cumulative total falls within a range of −120° to +120°.

In such a case, the parameter calculation unit 52 may calculate (select) one of two rotation angles in clockwise and counterclockwise rotations as parameter values regarding the rotation operation using any one of first to third methods described below.

As the first method, the parameter calculation unit 52 can calculate the rotation angle at which a direction from a dorsal side to a ventral side of a human body (or a direction from the ventral side to the dorsal side) is closer to an up direction of an image captured by the endoscope after the rotation operation according to the rotation angle among the two rotation angles in clockwise and counterclockwise rotations, as the parameter value regarding the rotation operation.

In this case, there are various method of specifying the rotation angle at which a direction from the dorsal side to the ventral side of the human body (or a direction from the ventral side to the dorsal side) is closer to the up direction of the image from among the two rotation angles. For example, a method of acquiring a direction vector on a three-dimensional image corresponding to an up direction of the image captured by the endoscope after the rotation operation according to the rotation angle with respect to each of the two rotation angles, calculating an inner product of the direction vector on the three-dimensional image and a direction vector directed from the dorsal side to the ventral side of the human body in the three-dimensional image, and specifying the rotation angle at which a value obtained by the calculation is small. Further, there is a method of obtaining the angle β in the up direction Eup of the image captured by the endoscope immediately after insertion into the bronchial tube with reference to the direction Bup from the dorsal side to the ventral side of the human body in the three-dimensional image, and specifying a rotation angle at which a sum of the angle β and a cumulative total of the rotation angles of the endoscope due to the rotation operation performed until the distal end portion of the endoscope arrives at the current position P(i) after the distal end portion of the endoscope is inserted into the bronchial tube falls within an angle range Rup from (−90−β)° to (+90−β)°.

Figure 7:
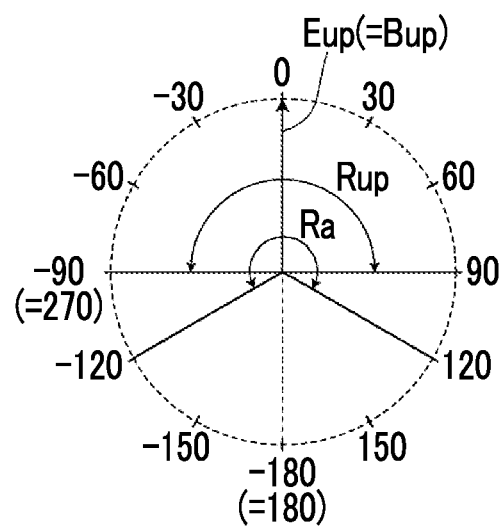
FIG. 7 is a diagram (part 1) illustrating a method of determining an angle of rotation on the basis of a direction of an image.

For example, as illustrated in FIG. 7, in a case where the predetermined angle range Ra is from −120° to +120° and the second angle range Rup is from −90° to +90° due to coincidence of the up direction Eup of the image captured by the endoscope in a state immediately after insertion into the bronchial tube with the direction Bup from the dorsal side to the ventral side of the human body in the three-dimensional image, the plane S can be caused to overlap the plane S(i), and in a case where there are two rotation angles of the endoscope of which a sum with the cumulative total falls within a range of −120° to +120°, the rotation angle at which a sum with the cumulative total further falls within −90° to +90° among the two rotation angles is calculated as the parameter value regarding the rotation operation.

Figure 8:
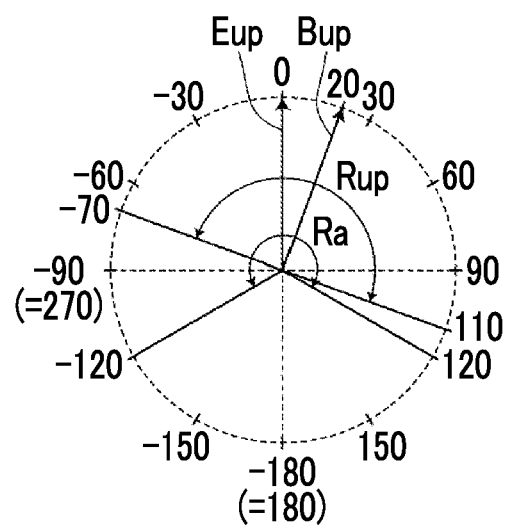
FIG. 8 is a diagram (part 2) illustrating a method of determining an angle of rotation on the basis of a direction of an image.

Further, in a case where the predetermined angle range Ra is from −120° to +120° and the second angle range Rup is from −70° to +110° due to the angle β of an up direction Eup of the image captured by the endoscope at an insertion start position with respect to a direction Bup from the dorsal side to the ventral side of the human body in the three-dimensional image being −20° as illustrated in FIG. 8, the plane S can be caused to overlap the plane S(i), and when there are two rotation angles of the endoscope of which the sum with the cumulative total falls within the range of −120° to +120°, the rotation angle at which the sum of cumulative total further falls within the range of −70° to +110° among the two rotation angles is calculated as the parameter value regarding the rotation operation.

As the second method, the parameter calculation unit 52 can calculate the rotation angle at which a direction directed from an inside to an outside of a human body is closer to an up direction of an image captured by the endoscope after an rotation operation according to the rotation angle among the two rotation angles in the clockwise direction and the counterclockwise direction, as the parameter value regarding the rotation operation. In this case, a method of specifying the rotation angle at which a direction directed from the inside to the outside of the human body is closer to the up direction of the image among the two rotation angles includes, for example, a method of first setting, in a three-dimensional image, a reference point at a position corresponding to a center (or a centroid) of a human body area included in the three-dimensional image, and then, specifying a rotation angle at which the set reference point exists in a lower portion among two divided portions in a case where, for each rotation angle, the three-dimensional image captured by the endoscope after the rotation operation according to the rotation angle is divided into two in a vertical direction.

As the third method, the parameter calculation unit 52 can calculate a rotation angle at which a sum of absolute values of second rotation angles at second positions, where the second position is a position where the endoscope advances from the first position in the course, is smaller between the two rotation angles in the clockwise direction and the counterclockwise direction, as a parameter value regarding the rotation operation.

The image generation unit 53 generates a virtual endoscopic image that is obtained by virtually imaging an inner wall of the bronchial tube included in the three-dimensional image by a virtual endoscope of which a position and a posture are defined by parameter values of the endoscope operation calculated by the parameter calculation unit 52 from the three-dimensional image. For the generation of the virtual endoscopic image, a known method such as a volume rendering method or a surface rendering method can be used. According to the image generation unit 53, it is possible to obtain not only the virtual endoscopic image of a still image at each position on the course C, but also a virtual endoscopic image of a moving image captured according to a movement of the endoscope along the course C.

The position information acquisition unit 54 acquires position information of the distal end of the endoscope detected by the position detection device 13.

The display control unit 55 displays navigation information for guiding the endoscope to a target position along a predetermined course in the bronchial tube on the display unit 7. The display control unit 55, specifically, can display a parameter value of the endoscope operation calculated by the parameter calculation unit 52, the virtual endoscopic image of the moving image or the still image generated by the image generation unit 53, and the like, as the navigation information, on the display unit 7. For example, the display control unit 55 can display the endoscopic image acquired from the endoscope device 1 in real time by the image acquisition unit 51 on the display unit 7 and can also display parameter values of an endoscope operation at a position of the distal end of the endoscope 11 acquired by the position information acquisition unit 54. Further, the display control unit 55 can display the virtual endoscopic image for navigating an endoscope operation at the position of the distal end of the endoscope 11 obtained by the position information acquisition unit 54 or a next endoscope operation on the display unit 7 instead of displaying the endoscopic image and the parameter values of the endoscope operation or in addition to the display. Of course, the parameter values of the endoscope operation may be displayed together on the display of the virtual endoscopic image.

Figure 9:
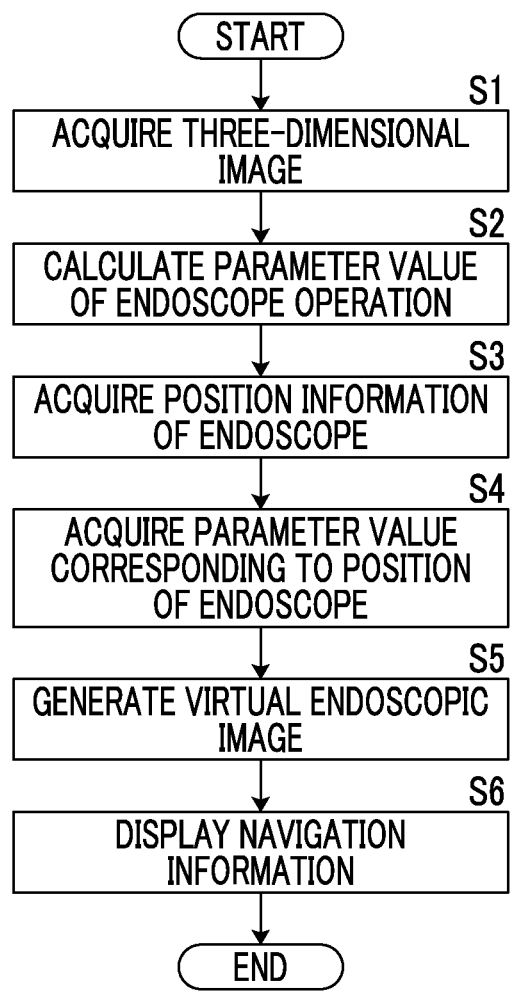
FIG. 9 is a flowchart illustrating a flow of a process performed by the image processing device of FIG. 1.

Next, an example of a flow of a process that is performed by the image processing device 4 will be described with reference to a flowchart illustrated in FIG. 9. First, the image acquisition unit 51 acquires the three-dimensional image obtained by imaging the chest portion including the bronchial tube from the image storage server 3 (S1). Then, the parameter calculation unit 52 calculates the parameter value regarding the endoscope operation for advancing the endoscope along a predetermined course in the bronchial tube from the three-dimensional image (S2). Specifically, the parameter calculation unit 52 first extracts a three-dimensional graph structure of a bronchial tube area included in the three-dimensional image through image analysis, sets the course C into which the endoscope is inserted in the extracted graph structure, and calculates parameter values regarding the advancing and retreating operation, the rotation operation, and the bending operation of the endoscope on the basis of information on the set course C. In particular, the parameter calculation unit 52 calculates a rotation angle around the axis of the endoscope for causing the plane S on which an operation of bending the endoscope can be performed to overlap the plane S(i) passing through positions of three points on the course C including an arbitrary position P(i), which is a rotation angle of which a sum with a cumulative total of the rotation angles of the endoscope due to the rotation operation performed until the distal end portion of the endoscope arrives at the current position P(i) after the distal end portion of the endoscope is inserted into the bronchial tube falls within a predetermined angle range Ra (for example, −90° to +90°), as the parameter of the rotation operation of the endoscope at the arbitrary position P(i) at which the endoscope is bent by a branch or the like on the course C.

Then, the position information acquisition unit 54 acquires the position information of the distal end of the endoscope detected by the position detection device 13 (S3), and the display control unit 55 acquires the parameter value of the endoscope operation corresponding to the position of the distal end of the endoscope 11 acquired by the position information acquisition unit 54 from among the parameter values regarding the endoscope operation calculated in step S2 (S4). Further, the image generation unit 53 generates a virtual endoscopic image for navigating the endoscope operation corresponding to the position of the distal end of the endoscope 11 acquired by the position information acquisition unit 54 from the three-dimensional image (S5). The display control unit 55 displays the information on the parameter value acquired in step S4 or the virtual endoscopic image acquired in step S5 on the display unit 7 (S6), and ends the process.

With the above configuration, in the image processing system of this embodiment, on the assumption that the endoscope is an endoscope in which an advancing and retreating operation in an axial direction, an operation of rotation around an axis, and an operation of bending a distal end portion only within one plane including an axis of the distal end portion are allowed, the parameter calculation unit 52 calculates the parameter value regarding the endoscope operation for advancing the endoscope along a predetermined course in the bronchial tube from the three-dimensional image representing the bronchial tube. Specifically, when one of a clockwise direction and a counterclockwise direction around the axis is set to positive, the other is set to negative, and a rotation angle of the endoscope due to the rotation operation at an arbitrary position on the course is calculated as a parameter value regarding the rotation operation, the rotation angle of the endoscope due to the rotation operation at the position of the target is calculated so that a sum of a cumulative total of rotation angles of the endoscope due to a rotation operation performed until the distal end portion arrives at the position of the target after the distal end portion is inserted into the bronchial tube, and the rotation angle of the endoscope due to the rotation operation at the position of the target falls within the predetermined angle range Ra. Thus, an appropriate angle range Ra for which a movable range of a wrist or the like is taken into consideration is determined in advance such that the rotation of the endoscope due to the rotation operation is performed only within the angle range Ra, and it is possible to reduce trouble of an operator gripping an endoscope again and improve operability.

In particular, in the image processing system of this embodiment, in a case where the angle range Ra is from −90° to +90°, it is possible to reduce trouble of the operator gripping an endoscope again and improve operability.

Although the case where the image processing device 4 includes the image generation unit 53, the position information acquisition unit 54, and the display control unit 55 has been described in the above embodiment, configurations thereof may be omitted, the parameter value regarding the endoscope operation may be calculated from the three-dimensional image acquired by the image acquisition unit 51, by the parameter calculation unit 52, and the calculated parameter value may be provided to be available to an external device.

In the above embodiment, the case where the image processing device, method, and program of the present invention are applied to the operation of the endoscope in the bronchial tube have been described, but the present invention is not limited thereto and the present invention can also be applied to a case where the endoscope is operated in another tubular structure having a branched structure, such as a vessel.

EXPLANATION OF REFERENCES

1: endoscope device
2: three-dimensional image capturing device
3: image storage server
4: image processing device
5: device body
5a: CPU
5b: memory
5c: HDD
6: input unit
7: display unit
11: endoscope
12: processor device
13: position detection device
51: image acquisition unit
52: parameter calculation unit
53: image generation unit
54: position information acquisition unit
55: display control unit

What is claimed is:

1. An image processing device for an endoscope in which predetermined operations are allowed, the predetermined operations being an advancing and retreating operation in an axial direction, an operation of rotation around an axis, and an operation of bending a distal end portion only within one endoscope bending plane including an axis of the distal end portion, the image processing device comprising:
a processor configured to:
acquire information of a course along which the endoscope travels in a luminal structure, the course being set based on a three-dimensional image indicating the luminal structure and including a plurality of branches, each of the plurality of branches representing a change in direction, and
calculate rotation angles of the endoscope for the operations of rotation at the plurality of branches, the rotation angles being angles for matching the one endoscope bending plane, which the distal end portion is allowed to bend, with a plane corresponding to the each of the plurality of branches,
wherein the processor calculates a first rotation angle at each branch for each of the plurality of branches such that a sum of the first rotation angle and a cumulative rotation angle fall within a predetermined angle range, the cumulative rotation angle being a total sum of rotation angles of the endoscope calculated for each of the branches from an entrance of the course to each branch.

2. The image processing device according to claim 1, wherein the predetermined angle range is from −90° to +90°, in a case where one of a clockwise direction and a counterclockwise direction around the axis is set to a positive angle and the other is set to a negative angle.

3. The image processing device according to claim 2, wherein the luminal structure is a luminal organ of a human body, and
in a case where two rotation angles for both the clockwise direction and the counterclockwise direction can fall within a predetermined angle, the processor is further configured to calculate one of the two rotation angles as the first rotation angle according to information of a direction vector from a dorsal side to a ventral side of the human body and an up direction vector of an image captured by the endoscope after the rotation operation with the first rotation angle.

4. The image processing device according to claim 2, wherein in a case where two rotation angles can be the first rotation angle, the processor is configured to calculate one of the two rotation angles as the first rotation angle so that an absolute value of a second rotation angle at a second branch is minimized, the second branch is a branch where the endoscope advances from the first branch along the course.

5. The image processing device according to claim 1, wherein the processor is further configured to:
acquire a position and a posture of the endoscope in the course; and
generate a virtual endoscopic image from the three-dimensional image using the position and the posture.

6. The image processing device according to claim 2, wherein the processor is further configured to:
acquire a position and a posture of the endoscope in the course; and
generate a virtual endoscopic image from the three-dimensional image using the position and the posture.

7. The image processing device according to claim 3, wherein the processor is further configured to:
acquire a position and a posture of the endoscope in the course; and generate a virtual endoscopic image from the three-dimensional image using the position and the posture.

8. The image processing device according to claim 1, wherein the processor is further configured to:
acquire a position and a posture of the endoscope in the course; and
generate a virtual endoscopic image from the three-dimensional image using the position and the posture.

9. The image processing device according to claim 4, wherein the processor is further configured to:
acquire a position and a posture of the endoscope in the course; and
generate a virtual endoscopic image from the three-dimensional image using the position and the posture.

10. The image processing device according to claim 1, wherein the processor is further configured to:
acquire a position of the endoscope in the course; and
display the first rotation angle on a display unit according to the position of the endoscope in the course when the endoscope advances along the course.

11. The image processing device according to claim 2, wherein the processor is further configured to:
acquire a position of the endoscope in the course; and
display the first rotation angle on a display unit according to the position of the endoscope in the course when the endoscope advances along the course.

12. The image processing device according to claim 3, wherein the processor is further configured to:
acquire a position of the endoscope in the course; and
display the first rotation angle on a display unit according to the position of the endoscope in the course when the endoscope advances along the course.

13. The image processing device according to claim 1, wherein the processor is further configured to:
acquire a position of the endoscope in the course; and
display the first rotation angle on a display unit according to the position of the endoscope in the course when the endoscope advances along the course.

14. The image processing device according to claim 4, wherein the processor is further configured to:
acquire a position of the endoscope in the course; and
display the first rotation angle on a display unit according to the position of the endoscope in the course when the endoscope advances along the course.

15. The image processing device according to claim 5, further comprising:
wherein the processor is further configured to:
acquire a position of the endoscope in the course; and
display the first rotation angle on a display unit according to the position of the endoscope in the course when the endoscope advances along the course.

16. An image processing method for an endoscope in which predetermined operations are allowed, the predetermined operations being an advancing and retreating operation in an axial direction, an operation of rotation around an axis, and an operation of bending a distal end portion only within one endoscope bending plane including an axis of the distal end portion, the image processing method comprising:
acquiring information of a course along which the endoscope travels in the luminal structure, the course being set based on a three-dimensional image indicating the luminal structure, and the course including a plurality of branches, each of the plurality of branches representing a change in direction; and
calculating rotation angles of the endoscope for the operations of rotation at each of the plurality of branches, the rotation angles being angles for matching the one endoscope bending plane, which the distal end portion is allowed to bend, with a plane corresponding to the each of the plurality of branches,
wherein a first rotation angle at each branch of the plurality of branches is calculated for each of the plurality of branches such that a sum of the first rotation angle and a cumulative rotation angle fall within a predetermined angle range, the cumulative rotation angle being a total sum of rotation angles of the endoscope calculated for each of the branches from an entrance of the course to each branch.

17. The image processing method according to claim 16, wherein the angle range is from −90° to +90°, in a case where one of a clockwise direction and a counterclockwise direction around the axis is set to a positive angle and the other is set to negative angle.

18. A non-transitory computer readable recording medium storing an image processing program for an endoscope in which predetermined operations are allowed, the predetermined operations being an advancing and retreating operation in an axial direction, an operation of rotation around an axis, and an operation of bending a distal end portion only within one endoscope bending plane including an axis of the distal end portion, the image processing program causing a computer to execute a process of:
acquiring information of a course along which the endoscope travels in the luminal structure, the course being set based on a three-dimensional image indicating the luminal structure, and the course including a plurality of branches, each of the plurality of branches representing a change in direction; and
calculating rotation angles of the endoscope for the operations of rotation at each of the plurality of branches, the rotation angles being angles for matching the one endoscope bending plane, which the distal end portion is allowed to bend, with a plane corresponding to the each of the plurality of branches,
wherein the first rotation angle is calculated for each branch of the plurality of branches such that a sum of the first rotation angle and a cumulative rotation angle fall within a predetermined angle range, the cumulative rotation angle being a total sum of rotation angles of the endoscope calculated for each of the plurality of branches from an entrance of the course to each branch.

19. The non-transitory computer readable recording medium according to claim 18,
wherein the angle range is from −90° to +90°, in a case where one of a clockwise direction and a counterclockwise direction around the axis is set to a positive angle and the other is set to negative angle.

* * * * *